US012714651B2

(12) United States Patent
Ito

(10) Patent No.: US 12,714,651 B2
(45) Date of Patent: Aug. 25, 2026

(54) ZIRCONIA COMPOSITION, PARTIALLY SINTERED MATERIAL AND SINTERED MATERIAL AND METHODS FOR PRODUCTION THEREOF, AND LAMINATE

(71) Applicant: KURARAY NORITAKE DENTAL INC., Okayama (JP)

(72) Inventor: Yoshihisa Ito, Miyoshi (JP)

(73) Assignee: KURARAY NORITAKE DENTAL INC., Okayama (JP)

( * ) Notice: Subject to any disclaimer, the term of this patent is extended or adjusted under 35 U.S.C. 154(b) by 468 days.

(21) Appl. No.: 18/384,007

(22) Filed: Oct. 26, 2023

(65) Prior Publication Data

US 2024/0050323 A1 Feb. 15, 2024

Related U.S. Application Data

(60) Division of application No. 17/226,571, filed on Apr. 9, 2021, now Pat. No. 11,890,359, which is a (Continued)

(30) Foreign Application Priority Data

Sep. 20, 2016 (JP) ................................ 2016-183130

(51) Int. Cl.
*C04B 35/486* (2006.01)
*A61C 5/70* (2017.01)
(Continued)

(52) U.S. Cl.
CPC ................ *A61K 6/818* (2020.01); *A61C 5/70* (2017.02); *A61C 13/083* (2013.01); *C01G 25/02* (2013.01); *C04B 35/486* (2013.01)

(58) Field of Classification Search
CPC .................. A61K 6/818; C04B 35/486; C04B 2235/3225; C04B 2235/528;
(Continued)

(56) References Cited

U.S. PATENT DOCUMENTS 9,193,630 B2 * 11/2015 Bocciarelli ......... C04B 35/4885
10,231,807 B2 3/2019 Yamada et al.
(Continued)

FOREIGN PATENT DOCUMENTS

EP 2 995 434 A1 3/2016
EP 3 272 724 A1 1/2018
(Continued)

OTHER PUBLICATIONS

Extended European Search Report issued on Apr. 17, 2020 in Patent Application No. 17853101.8, 8 pages.
(Continued)

*Primary Examiner* — Noah S Wiese
(74) *Attorney, Agent, or Firm* — Oblon, McClelland, Maier & Neustadt, L.L.P.

(57) ABSTRACT

A composition may include granules in which zirconia particles are aggregated. The granules may have an average circularity of 0.81 or greater based on a projected image. The zirconia crystal system of the zirconia particles may be 20% or more monoclinic. An angle of repose of the composition, measured in accordance with JIS R9301-2-2, may be in a range of from 20 degrees to 35 degrees.

20 Claims, 5 Drawing Sheets

Related U.S. Application Data continuation of application No. 16/330,917, filed as application No. PCT/JP2017/033981 on Sep. 20, 2017, now Pat. No. 11,033,467.

(51) Int. Cl.

| | |
|---|---|
| ***A61C 13/083*** | (2006.01) |
| ***A61K 6/818*** | (2020.01) |
| ***C01G 25/02*** | (2006.01) |

(58) Field of Classification Search

CPC .... C04B 2235/5296; C04B 2235/5436; C04B 2235/5445; C04B 2235/76; C04B 2235/762; C04B 2235/348; C04B 2235/62695; C04B 2235/602

See application file for complete search history.

(56) References Cited

U.S. PATENT DOCUMENTS

| | | | |
|---|---|---|---|
| 10,512,527 | B2 | 12/2019 | Yamada et al. |
| 2016/0074142 | A1* | 3/2016 | Yamada .................... B28B 5/00 264/72 |
| 2019/0151055 | A1 | 5/2019 | Yamada et al. |

FOREIGN PATENT DOCUMENTS

| | | | |
|---|---|---|---|
| JP | 2004-338998 | A | 12/2004 |
| JP | 2006193345 | A * | 7/2006 |
| JP | 2010-150063 | A | 7/2010 |
| JP | 2013-100222 | A | 5/2013 |
| JP | 2014-218418 | A | 11/2014 |
| KR | 10-2016-0007574 | A | 1/2016 |
| WO | 2014/181828 | A1 | 11/2014 |
| WO | 2016/147681 | A1 | 9/2016 |
| WO | 2017/042611 | A1 | 3/2017 |

OTHER PUBLICATIONS

International Search Report issued on Nov. 28, 2017, in PCT/JP2017/033981 filed on Sep. 20, 2017.

Office Action issued Mar. 19, 2021 in corresponding European Patent Application No. 17853101.8 (with English Translation), 29 pages.

Korean Office Action issued Nov. 16, 2021 in Korean Patent Application No. 10-2019-7008071 (with English machine translation), 17 pages.

* cited by examiner

[Figure 1]

[Figure 2]
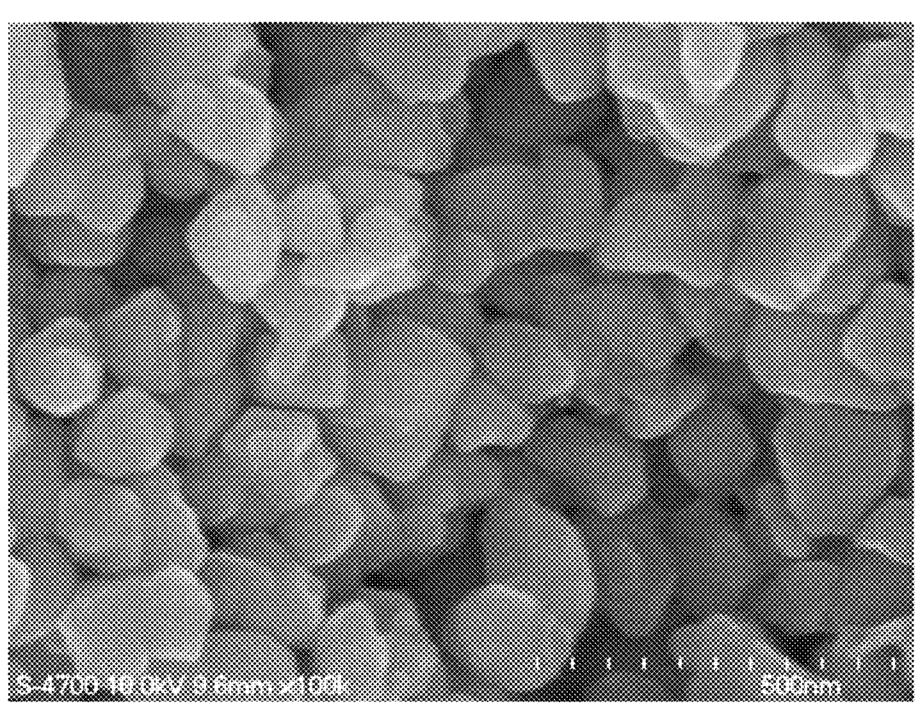

[Figure 3]
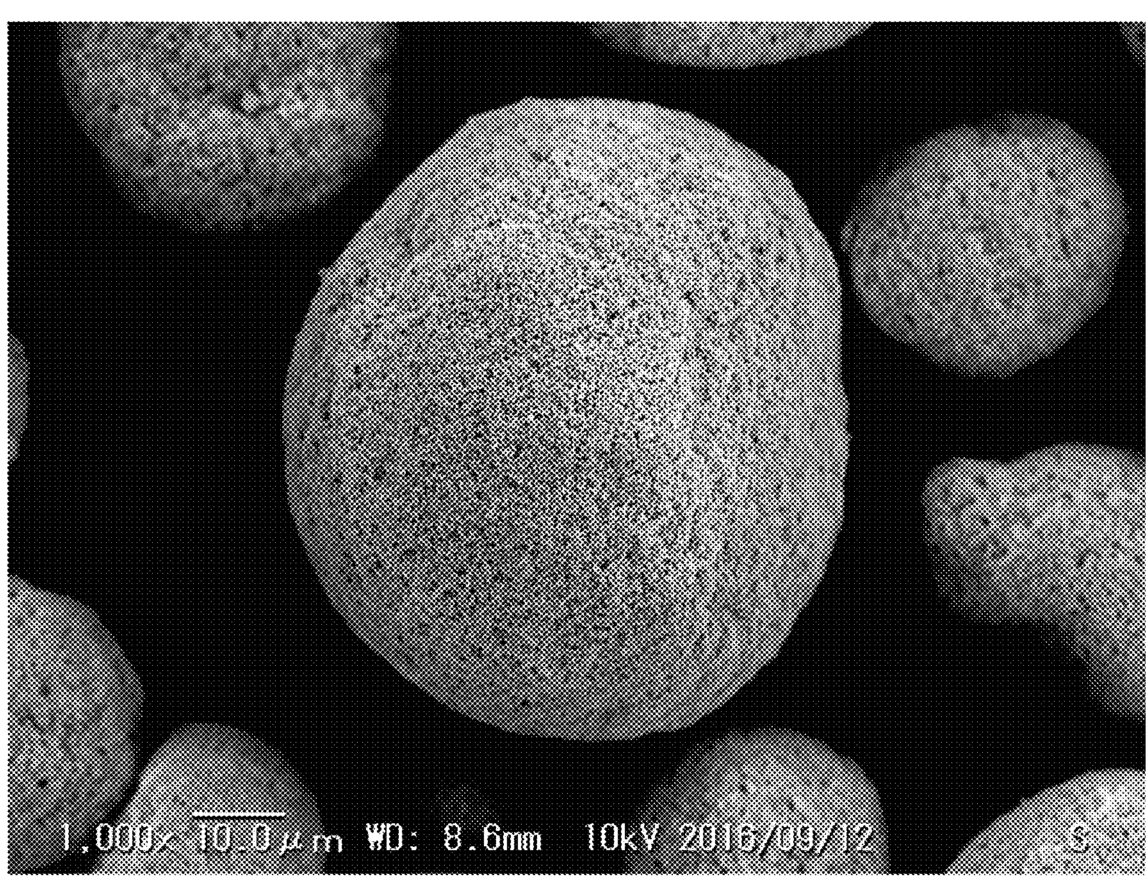

[Figure 4]
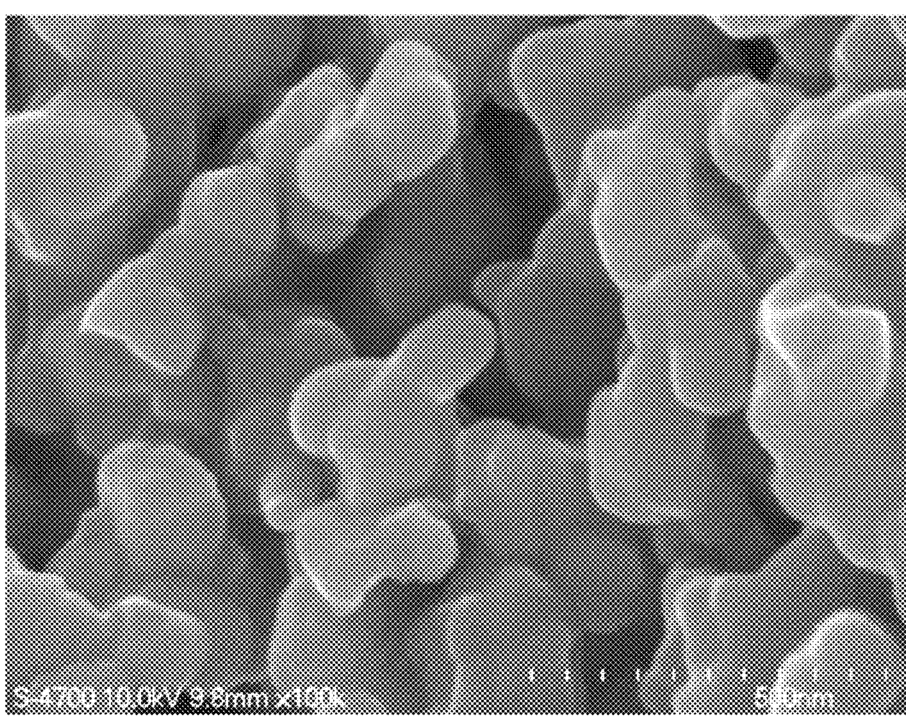
[Figure 5]
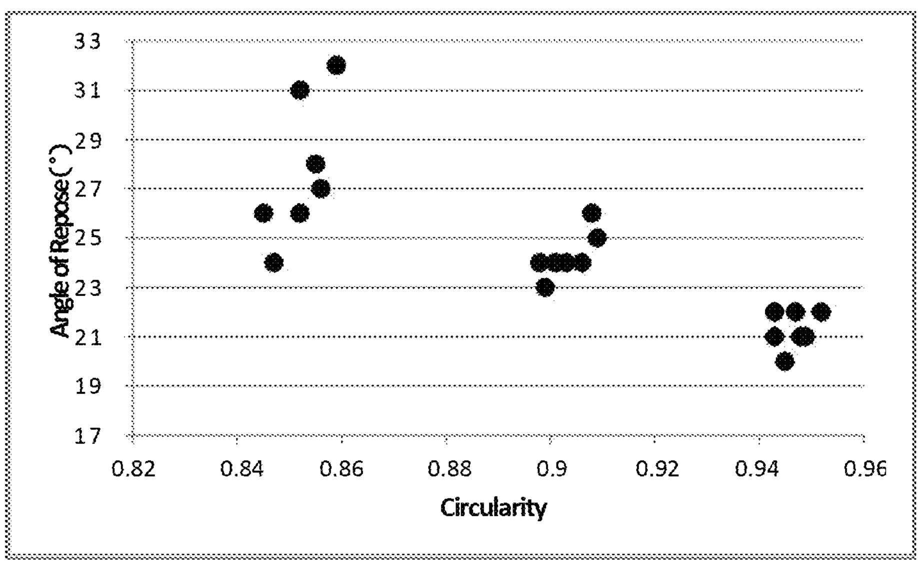

[Figure 6]
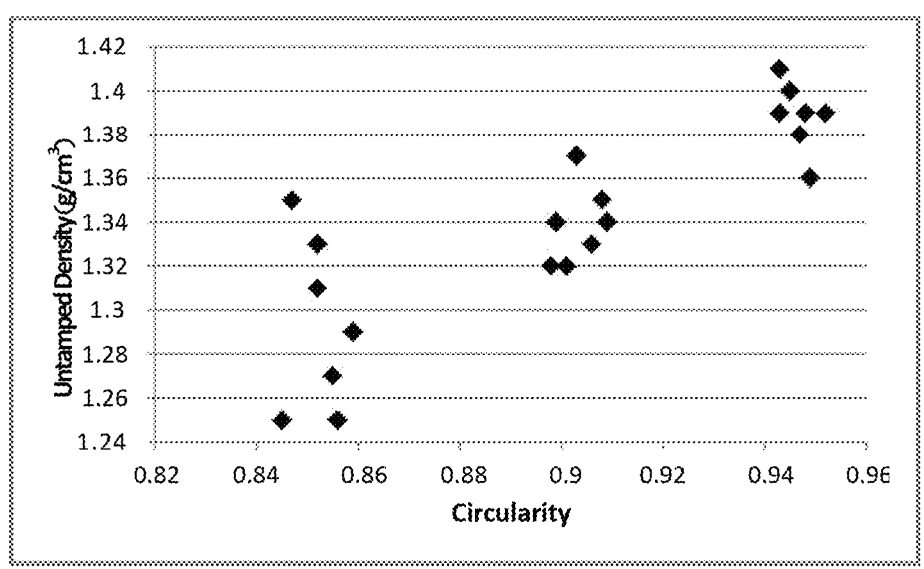
[Figure 7]
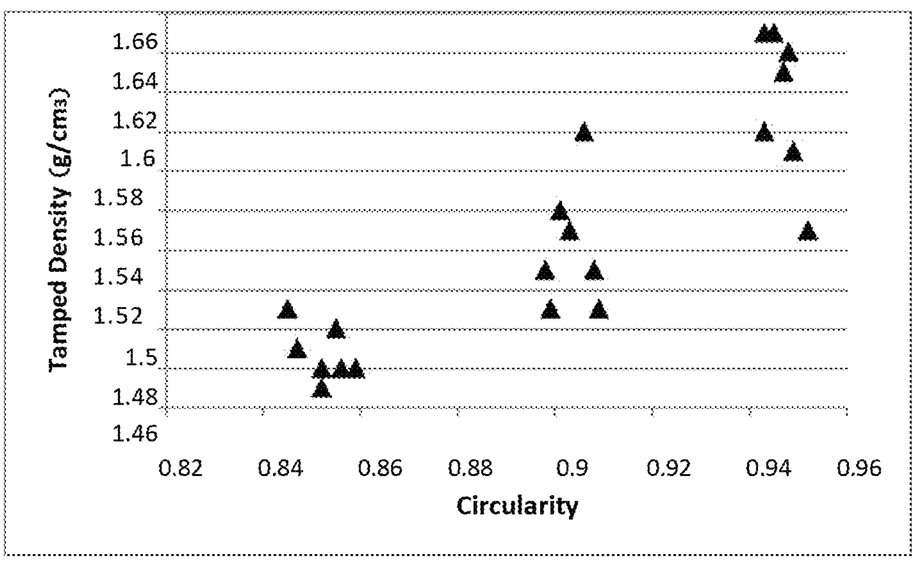

ZIRCONIA COMPOSITION, PARTIALLY SINTERED MATERIAL AND SINTERED MATERIAL AND METHODS FOR PRODUCTION THEREOF, AND LAMINATE

CROSS-REFERENCE TO RELATED APPLICATIONS

The present application is a continuation of U.S. Ser. No. 17/226,571, filed on Apr. 9, 2021, and published on Oct. 7, 2021, as US 2021/0308018 A1, which was a continuation of U.S. Ser. No. 16/330,917, filed on Mar. 20, 2019, and published on Aug. 8, 2019, as US 2019/0231651 A1, now U.S. Pat. No. 11,033,467, which was the national stage of PCT/JP2017/033981, filed Sep. 20, 2017, and published on Mar. 29, 2018, as WO 2018/056331 A1, and claims the benefit of the priority of Japanese Patent Application No. 2016-183130, filed on Sep. 20, 2016, the disclosure of each of which is incorporated by reference herein in its entirety.

FIELD OF THE INVENTION

The present disclosure relates to a composition predominantly containing zirconia (zirconium oxide (IV); $ZrO_2$) in the form of a granule, and a method of producing the same. The present disclosure relates to a zirconia pre-sintered body and sintered body, and a production method thereof. The present disclosure also relates to a layered body of granules.

BACKGROUND OF THE INVENTION

A zirconia sintered body formed by sintering zirconia powder has a high strength, and therefore, it is used in various applications. For example, the zirconia sintered body is applied to dental materials, tools, components, and the like.

In general, such a zirconia sintered body is produced by firing a shaped zirconia powder (for example, see Patent Literature 1). Patent Literature 1 discloses a process for producing a translucent zirconia sintered body, the process including molding the zirconia powder that is a spray-shaped powder granule and then sintering the resultant body at 1350-1450° C. at normal pressure, the zirconia powder containing 2-4 mol % yttria as a stabilizer, less than 0.1 wt % alumina as an additive, and an organic binder.

Patent Literature 2 discloses a zirconia sintered body produced by layering a plurality of zirconia powders different in composition.

CITATION LIST

Patent Literature

[PATENT LITERATURE 1] Japanese Patent Application Laid-Open No. 2010-150063

[PATENT LITERATURE 2] Japanese Patent Application Laid-Open No. 2014-218418

DISCLOSURE OF THE INVENTION

Problem to be Solved by the Invention

In general, granules, as described in Patent Literature 1, are produced via a spray drying method. For example, powder containing additives is produced by adding additives, such as a binder, to slurry in which powder is dispersed in a solvent, such as water, and drying this slurry using a spray drying device (spray dryer). In the powder dried via a spray drying method, an aggregate of particles (granulated body) constitutes one particle. The granule described in Patent Literature 1 is an aggregate of a plurality of zirconia particles, too. Hereinafter, an aggregate of particles (granulated body), formed via a spray drying method, is referred to as a "granule." In general, a granule has a spherical shape.

The sintered body, as described in Patent Literature 2, is produced by, for example, firing a shaped body that has been formed by layering powders in the form of a granule different in composition into a mold. However, unless the granules of adjacent layers are partially mixed at the boundary between the layers upon the production of the sintered body, detachment at the boundary surface between the layers, and distortion and breakage due to distortion may occur in the sintered body. In addition, when colors of the layers are different in order to create gradation, unless the granules of the adjacent layers are partially mixed, the change in color over the boundary is too clear in the appearance of the sintered body, and thus it is impossible to create gradation. These phenomena emerge more notably when the powder of each layer is produced independently, and when the composition of each layer is made different from each other. Therefore, it is preferred that the partial mixing of granules can be promoted between adjacent layers upon the layering of the powders.

Means to Solve the Problem

According to a first aspect of the present disclosure, a composition is provided, the composition comprising granules in which zirconia particles are aggregated. The granules have an average circularity of 0.81 or greater based on a projected image.

According to a second aspect of the present disclosure, a layered body is provided, the layered body comprising a first layer and a second layer that comprise granules and are adjacent to each other. The granules in the first layer have an average circularity of 0.70 or smaller based on a projected image. The granules in the second layer have an average circularity of 0.92 or greater based on a projected image.

According to a third aspect of the present disclosure, a layered body is provided, the layered body comprising a first layer and a second layer that comprise granules and are adjacent to each other. The granules in the first layer have an average circularity of greater than 0.70 and smaller than 0.81 based on a projected image. The granules in the second layer have an average circularity of 0.86 or greater based on a projected image.

According to a fourth aspect of the present disclosure, a layered body is provided, the layered body comprising a first layer and a second layer that comprise granules and are adjacent to each other. The granules in the first layer and the second layer have an average circularity of 0.81 or greater based on a projected image.

According to a fifth aspect of the present disclosure, a pre-sintered body is provided, the pre-sintered body being produced by firing the layered body according to any one of the second to fourth aspects at a temperature of 800° C. to 1200° C.

According to a sixth aspect of the present disclosure, a sintered body is provided, the sintered body being produced by firing the pre-sintered body according to the fifth aspect at a temperature of 1400° C. to 1600° C.

According to a seventh aspect of the present disclosure, a sintered body is provided, the pre-sintered body being produced by firing the layered body according to any one of the second to fourth aspects at a temperature of 1400° C. to 1600° C.

According to an eighth aspect of the present disclosure, a method of producing a composition is provided, the method comprising a dispersion step of dispersing a composition in a solvent, the composition comprising zirconia particles predominantly including primary particles having an average particle diameter of 0.01 μm to 2.5 μm in a solvent, and a drying step of drying the composition via a spray drying method to produce granules in which the zirconia particles are aggregated.

According to a ninth aspect of the present disclosure, a method of producing a zirconia pre-sintered body is provided, the method comprising a first shaping step of shaping the composition according to the first aspect, the layered body according to any one of the second to fourth aspects, or a composition produced by the method of producing a composition according to the eighth aspect to produce a first shaped body, and a pre-sintering step of firing the first shaped body at a temperature not leading to sintering to produce a pre-sintered body.

According to a tenth aspect of the present disclosure, a method of producing a zirconia sintered body is provided, the method comprising a shaping step of shaping the composition according to the first aspect, the layered body according to any one of the second to fourth aspects, or a composition produced by the method of producing a composition according to the eighth aspect to produce a first shaped body, and a sintering step of firing the first shaped body at a temperature allowing sintering or higher to produce a sintered body.

According to a eleventh aspect of the present disclosure, a method of producing a zirconia sintered body is provided, the method comprising a sintering step of firing the pre-sintered body according the fifth aspect or a pre-sintered body produced by the method of producing a zirconia pre-sintered body according the ninth aspect at a temperature allowing sintering or higher to produce a sintered body.

Effect of the Invention

According to the present disclosure, when a sintered body produced by layering powders, in particular, a layered body is produced with powders that have been produced separately, or even when a layered body is produced with powders different in composition, the occurrence of detachment between the layers or defects can be suppressed. In addition, when gradation is created, the change in color between layers can be made smooth.

BRIEF DESCRIPTION OF THE DRAWINGS

FIG. 1 is a scanning electron micrograph of a granule of a composition of the present disclosure.

FIG. 2 is a scanning electron micrograph of particles constituting the granule shown in FIG. 1.

FIG. 3 is a scanning electron micrograph of a granule of a composition in a comparative example.

FIG. 4 is a scanning electron micrograph of particles constituting the granule shown in FIG. 3.

FIG. 5 is a graph on which the angle of repose is plotted against the circularity in Examples 19 to 39.

FIG. 6 is a graph on which the untamped density is plotted against the circularity in Examples 19 to 39.

FIG. 7 is a graph on which the tamped density is plotted against the circularity in Examples 19 to 39.

DESCRIPTION OF THE PREFERRED EMBODIMENT

According to a preferred mode of the above first aspect, an angle of repose measured in accordance with JIS R9301-2-2 is 20 degrees to 35 degrees.

According to a preferred mode of the above first aspect, an untamped density measured in accordance with JIS R9301-2-3 is 1.2 g/cm$^3$ or more.

According to a preferred mode of the above first aspect, a tamped density measured in accordance with JIS R9301-2-3 is 1.3 g/cm$^3$ or more.

According to a preferred mode of the above first aspect, an average particle diameter of the zirconia particles is 0.01 μm to 2.5 μm.

According to a preferred mode of the above first aspect, a BET specific surface area of the zirconia particles is 7.5 m$^2$/g to 25 m$^2$/g.

According to a preferred mode of the above first aspect, an average particle diameter of the granules is 10 μm to 200 μm.

According to a preferred mode of the above first aspect, the composition further comprises a stabilizer capable of suppressing phase transition of zirconia.

According to a preferred mode of the above first aspect, a portion of the stabilizer does not form a solid solution with zirconia. A monoclinic system accounts for 20% or more of a crystal system of zirconia.

According to a preferred mode of the above first aspect, the stabilizer is yttria.

According to a preferred mode of the above first aspect, the composition comprises 3 mol % to 7.5 mol % of yttria based on a total amount of moles of zirconia and yttria.

According to a preferred mode of the above first aspect, the composition further comprises a binder and/or a dispersing agent.

According to a preferred mode of at least any one of the above second to fourth aspects, the first layer and the second layer are different in composition.

According to a preferred mode of at least any one of the above second to fourth aspects, an average particle diameter of the granules is 10 μm to 200 μm.

According to a preferred mode of at least any one of the above second to fourth aspects, the granules are granules in which zirconia particles are aggregated.

According to a preferred mode of the above eighth aspect, the method of producing a composition further comprises a pulverization step of pulverizing the composition such that an average particle diameter of the zirconia particles is 0.01 μm to 2.5 μm, prior to the drying step.

According to a preferred mode of the above eighth aspect, in the dispersion step, a stabilizer capable of suppressing phase transition of zirconia is mixed into the composition.

According to a preferred mode of the above eighth aspect, the stabilizer is yttria.

According to a preferred mode of the above eighth aspect, yttria is added such that an yttria content is 3 mol % to 7.5 mol % based on a total amount of moles of zirconia and yttria.

According to a preferred mode of the above eighth aspect, the method of producing a composition further comprises a step of putting a first layer into a mold, the first layer having a first composition of the composition, a step of layering a second layer onto the first layer, the second layer having a second composition of the composition, and a step of vibrating the mold.

According to a preferred mode of the above eighth aspect, granules in one layer of the first layer and the second layer have an average circularity of 0.70 or smaller based on a projected image. Granules in the other layer of the first layer and the second layer have an average circularity of 0.92 or greater based on a projected image.

According to a preferred mode of the above eighth aspect, granules in one layer of the first layer and the second layer have an average circularity of greater than 0.70 and smaller than 0.81 based on a projected image. Granules in the other layer of the first layer and the second layer have an average circularity of 0.86 or greater based on a projected image.

According to a preferred mode of the above eighth aspect, granules in the first layer and the second layer have an average circularity of 0.81 or greater based on a projected image.

According to a preferred mode of the above eighth aspect, the first composition and the second composition are different.

According to a preferred mode of the above ninth aspect, the first shaped body is fired at a temperature of 800° C. to 1200° C. in the pre-sintering step.

According to a preferred mode of the above eleventh aspect, the method of producing a zirconia sintered body further comprises a shaping step of shaping the pre-sintered body to produce a second shaped body. The second shaped body is fired as the pre-sintered body to produce the sintered body in the sintering step.

As a first embodiment, a composition of the present disclosure will be described. The composition may be a precursor (intermediate product) for a zirconia sintered body and pre-sintered body.

The composition can contain zirconia as the predominant component. The composition can be in the form of powder. Powder may be a mass of granules. A granule is formed of aggregated primary particles and/or secondary particles which are formed of aggregated primary particles.

The granule is a mass (aggregate) of particles. When the composition takes the form of a granule, in order to distinguish a particle from a granule, the expressions "particle" and "particle constituting a granule" will be used hereinafter. The "particle constituting a granule" includes a zirconia particle and a stabilizer particle.

In the present disclosure, a "primary particle" refers to a globe-shaped particle, which is the minimum unit. For example, a primary particle refers to a globe-shaped body that does not bind to another particle and appears to be in a separable condition, when observed by an electron microscope. In the present disclosure, a "secondary particle" refers to a particle in a condition where particles that appear to be primary particles in an electron microscope aggregate. The secondary particle includes an aggregate in which primary particles are attached in a breakable manner, as well as an aggregate that appears to be one particle in which primary particles are fused and attached one another in an inseparable manner. In many cases, in an electric microscope image, the secondary particle is not a globe-shaped body and has a distorted shape.

It is preferred that particles constituting a granule be predominantly primary particles. For example, in the visual checking of an electron microscope image, it is preferred that the number of primary particles be bigger than the number of secondary particles. For example, in the visual checking of an electron microscope image, it is preferred that 50% or more, preferably 70% or more, and more preferably 80% or more of primary particles out of the primary particles (including primary particles constituting secondary particles) be particles not constituting secondary particles. Since secondary particles normally have irregular shapes, when the number of secondary particles gets bigger, the circularity of the granule, mentioned below, will become lower.

The average particle diameter of the particles constituting a granule is preferably 0.06 μm or greater, more preferably 0.01 μm or greater, more preferably 0.05 μm or greater, more preferably 0.08 μm or greater, more preferably 0.10 μm or greater, and further preferably 0.11 μm or greater, as measured via laser diffraction/scattering particle size distribution measuring method. In addition, the average particle diameter is preferably 2.5 μm or smaller, more preferably 1.5 μm or smaller, more preferably 1 μm or smaller, more preferably 0.6 μm or smaller, more preferably 0.3 μm or smaller, more preferably 0.15 μm or smaller, more preferably 0.14 μm or smaller, and further preferably 0.13 μm or smaller. The average particle diameter herein means a particle diameter measured with no distinction between primary particles and secondary particles. By making the average particle diameter smaller, the circularity of the granule, mentioned below, can be increased.

When particles or granules are made without undergoing the firing step, in order to further enhance the translucency of the sintered body produced from the particles or granules, the average particle diameter of the particles constituting a granule is more preferably less than 0.13 μm, more preferably 0.125 μm or smaller, more preferably 0.12 μm or smaller, and further preferably 0.115 μm or smaller.

The BET specific surface area of the particles constituting a granule is, when measured in accordance with JIS Z8830 (2013), preferably 7.0 $m^2/g$ or more, more preferably 7.5 $m^2/g$ or more, and further preferably 8 $m^2/g$ or more. When the BET specific surface area is less than 7.0 $m^2/g$, the sintering may be difficult, or even if the sintering becomes possible, the sintered body may become clouded. In addition, the BET specific surface area is preferably 30 $m^2/g$ or less, more preferably 25 $m^2/g$ or less, and further preferably 20 $m^2/g$ or less. When the BET specific surface area exceeds 30 $m^2/g$, the composition becomes susceptible to the temperature unevenness in the firing furnace. In addition, when the firing time for sintering is shortened, the translucency of the sintered body declines. The BET specific surface area herein means a specific surface area measured with no distinction between primary particles and secondary particles.

It is preferred that, among zirconia in the zirconia composition, 50% or more, preferably 70% or more, more preferably 80% or more, and further preferably 90% or more of zirconia forms granules.

The average particle diameter of the granule in the zirconia composition is preferably 10 μm or greater, more preferably 12 μm or greater, and further preferably 14 μm or greater. If the average particle diameter of the granule is less than 10 μm, the air is involved in the granules when the granules are put into a mold, and thus there is a possibility of insufficient degassing upon shaping, thereby not being able to produce a uniform and compact shaped body. Moreover, there is a possibility that the granules are emitted from a gap upon shaping, thereby producing a shaped body that does not satisfy a predetermined, required amount. The average particle diameter of the granule is preferably 200 μm or smaller, more preferably 190 μm or smaller, more preferably 180 μm or smaller, more preferably 150 μm or smaller, and further preferably 100 μm or smaller. When the average particle diameter of the granule exceeds 200 μm, cavities are formed readily inside the granule. In addition, when granules are placed into the mold, gaps are likely to occur. Due to these phenomena, there is a possibility of insufficient degassing upon shaping, thereby not being able to produce a compact shaped body. There is also a possibility that shrinkage proceeds too much upon shaping, thereby not being able to produce a shaped body having a desired size. Among zirconia in the zirconia composition, it is preferred that 50% or more of zirconia constitutes granules. It is preferred that the average particle diameter of the granule be measured by a method in which granules are not destroyed. For example, the average particle diameter of the granule can be measured via oscillating type and ro-tap type particle size distribution measuring method or acoustic wave vibration sieving type particle size distribution measuring method (for example, with the use of Robot Sifter from SEISHIN ENTERPRISE Co., Ltd.).

It is preferred that the sphericity of the granule be high. By increasing the sphericity of the granule, when zirconia powders having different compositions are layered, mixing at the interface between layers can be brought about. Moreover, when zirconia powder is filled in a mold to produce a shaped body, those having a higher sphericity can increase the filling density even with the same average particle diameter. By increasing the filling density, the strength and the translucency of the sintered body can be enhanced. In addition, even if the mold has a corner part, the filling property of the granule to the corner part can also be enhanced.

The sphericity of the granule can be expressed with, for example, circularity based on a projected image, angle of repose, untamped density, tamped density, etc.

The average circularity based on a projected image of the granule in the zirconia composition is preferably 0.81 or higher, more preferably 0.85 or higher, more preferably 0.90 or higher, and further preferably 0.95 or higher. The circularity can be calculated as a ratio of the perimeter of the circle that has the same area as the granule, in terms of its projected image, to the perimeter of the granule. That is, the circularity can be calculated from the following equation. It is preferred that the average circularity be the average value of circularities of 10,000 or more granules. Circularity=(perimeter (circumference) of circle having the same area as granule)/perimeter of granule The angle of repose of the zirconia composition is preferably 35° or less, more preferably 32° or less, more preferably 28° or less, more preferably 26° or less, and further preferably 24° or less. The angle of repose can be measured in accordance with JIS R9301-2-2.

The untamped density of the zirconia composition is preferably 1.0 $g/cm^3$ or higher, more preferably 1.1 $g/cm^3$ or higher, more preferably 1.2 $g/cm^3$ or higher, and further preferably 1.3 $g/cm^3$ or higher. The untamped density can be measured in accordance with JIS R9301-2-3.

The tamped density of the zirconia composition is preferably 1.3 $g/cm^3$ or higher, more preferably 1.4 $g/cm^3$ or higher, and further preferably 1.5 $g/cm^3$ or higher. The tamped density can be measured in accordance with JIS R9301-2-3.

The zirconia composition may further contain a stabilizer capable of suppressing phase transition of zirconia. It is preferred that the stabilizer be capable of forming partially-stabilized zirconia. Examples of the stabilizer may include oxides, such as calcium oxide (CaO), magnesium oxide (MgO), yttrium oxide ($Y_2O_3$; referred to as "yttria" hereinafter), cerium oxide ($CeO_2$), and scandium oxide ($Sc_2O_3$). The content of the stabilizer in the composition, pre-sintered body and sintered body can be measured via, for example, inductively coupled plasma (ICP) emission spectral analysis, fluorescent X-ray analysis and the like.

In the zirconia composition, all of the stabilizer may form a solid solution with zirconia, or a portion of the stabilizer may form a solid solution with zirconia. For example, an X-ray diffraction (XRD) pattern may be used to confirm that a portion of the stabilizer does not form a solid solution with zirconia. In the XRD pattern of the composition, when a peak resulting from the stabilizer is found, this means that the stabilizer exists without forming a solid solution with zirconia in the composition. When the entire amount of the stabilizer forms a solid solution with zirconia, basically, a peak resulting from the stabilizer cannot be found in the XRD pattern. However, depending on conditions, such as crystalline state of the stabilizer, the stabilizer may not form a solid solution with zirconia even when there is no peak of the stabilizer found in the XRD pattern. If the predominant crystal system of zirconia is tetragonal and/or cubic and there is no peak of the stabilizer found in the XRD pattern, then it is believed that the majority, basically all, of the stabilizer forms a solid solution with zirconia.

In the composition of the present disclosure, all of the stabilizer is allowed not to form a solid solution with zirconia.

Note that, in the present disclosure, that the stabilizer forms a solid solution with zirconia refers to, for example, that an element (atom) contained in the stabilizer forms a solid solution with zirconia.

From the viewpoint of strength and translucency of the sintered body produced from the composition of the present disclosure, it is preferred that the stabilizer be yttria. The content by percentage of yttria is preferably 3 mol % or more, more preferably 3.5 mol % or more, and further preferably 4 mol % or more based on the total amount of moles of zirconia and yttria. When the content of yttria is 3 mol % or more, the translucency of the sintered body can be enhanced. In addition, the content by percentage of yttria is preferably 7.5 mol % or less, more preferably 7 mol % or less, more preferably 6.5 mol % or less, and further preferably 6 mol % or less based on the total amount of moles of zirconia and yttria. When the content of yttria is 7.5 mol % or less, it is possible to suppress decline of the strength of the sintered body.

The abundance by percentage of yttria that does not form a solid solution with zirconia (hereinafter referred to as "not-doped yttria (free yttria)") in the composition, $f_y$, can be calculated based on the following Expression 1. The abundance $f_y$ of not-doped yttria is preferably greater than 0%, more preferably 1% or more, more preferably 2% or more, and further preferably 3% or more. The upper limit of the abundance $f_y$ of not-doped yttria depends on the content of yttria in the composition. When the content of yttria is 7.5 mol % or less based on the total amount of moles of zirconia and yttria, $f_y$ can be 15% or less. For example, when the content of yttria is 3.5 mol % to 4.5 mol %, $f_y$ can be 7% or less. When the content of yttria is 5 mol % to 6 mol %, $f_y$ can be 10% or less. When the content of yttria is 5.5 mol % to 6.5 mol %, $f_y$ can be 11% or less.

When the content by percentage of yttria is 3 mol % or more and less than 4.5 mol % in the composition, $f_y$ is preferably 2% or more, more preferably 3% or more, more preferably 4% or more, and further preferably 5% or more. When the content of yttria is 4.5 mol % or more and less than 5.8 mol %, $f_y$ is preferably 3% or more, more preferably 4% or more, more preferably 5% or more, more preferably 6% or more, and further preferably 7% or more. When the content of yttria is 5.8 mol % or more and 7.5 mol % or less, $f_y$ is preferably 4% or more, more preferably 5% or more, more preferably 6% or more, more preferably 7% or more, and further preferably 8% or more.

$$f_y(\%) = \frac{I_y(111)}{I_y(111) + I_m(111) + I_m(11-1) + I_t(111) + I_c(111)} \times 100 \quad \text{[Expression 1]}$$

In Expression 1, $I_y$ (111) represents a peak intensity of plane (111) of yttria in the vicinity of 2θ=29° in an XRD pattern using CuKα radiation. $I_m$ (111) and $I_m$ (11-1) represent peak intensities of plane (111) and plane (11-1) of monoclinic zirconia, respectively. $I_t$ (111) represents a peak intensity of plane (111) of tetragonal zirconia. $I_c$ (111) represents a peak intensity of plane (111) of cubic zirconia.

Expression 1 described above can also be applied to calculation of the abundance of a not-doped stabilizer other than yttria, by substituting another peak instead of $I_y$ (111).

It is preferred that the predominant crystal system of zirconia in the composition be monoclinic. In the composition, the percentage of monoclinic system in zirconia, $f_m$, is preferably 20% or more, preferably 30% or more, preferably 40% or more, preferably 50% or more, preferably 60% or more, more preferably 70% or more, more preferably 80% or more, more preferably 85% or more, more preferably 90% or more, and further preferably 95% or more based on the total amount of monoclinic system, tetragonal system and cubic system. The percentage of monoclinic system $f_m$ can be calculated from the following Expression 2, based on an XRD peak using CuKα radiation. The meaning of each symbol in Expression 2 is the same as in Expression 1. The predominant crystal system in the composition possibly contributes to elevation of the shrinkage temperature and shortening of sintering time.

In the composition of the present disclosure, the peaks of tetragonal and cubic crystals are allowed not to be detected substantially. That is, the percentage of monoclinic system $f_m$ may be 100%.

$$f_m(\%) = \frac{I_m(111) + I_m(11-1)}{I_m(111) + I_m(11-1) + I_t(111) + I_c(111)} \times 100 \quad \text{[Expression 2]}$$

When a pressed body of the composition is fired at 800° C. or higher and 1000° C. or lower to produce a pre-sintered body, it is preferred that a shrinkage factor from the pressed body to the pre-sintered body be 1% or less relative to the unidirectional dimension of the pressed body. In addition, when a pressed body of the composition is fired at higher than 1000° C. and 1200° C. or lower to produce a pre-sintered body, it is preferred that a shrinkage factor from the pressed body to the pre-sintered body be 5% or less relative to the unidirectional dimension of the pressed body. Note that the pressed body here is made by pressing zirconia powder with a pressure of 300 kg/cm$^2$ to produce a molded body and then further by subjecting the molded body to the CIP (Cold Isostatic Pressing) process at 1700 kg/cm$^2$.

The composition may contain additives other than zirconia and yttria. Examples of additives may include pigments (including coloring agents and fluorescent agents), binders, dispersing agents, anti-foaming agents, alumina ($Al_2O_3$), titanium oxide ($TiO_2$), silica ($SiO_2$), and the like.

Examples of additives, such as coloring agents, may include oxides of at least one element selected from the group of Ti, V, Cr, Mn, Fe, Co, Ni, Zn, Y, Zr, Sn, Sb, Bi, Ce, Pr, Sm, Eu, Gd, Tb, and Er. Examples of fluorescent agents may include $Y_2SiO_5$:Ce, $Y_2SiO_5$:Tb, (Y,Gd,Eu)$BO_3$, $Y_2O_3$:Eu, YAG:Ce, $ZnGa_2O_4$:Zn, $BaMgAl_{10}O_{17}$:Eu, and the like.

As binders, organic binders can be used. For example, acrylic-based, acrylate-based, paraffin-based, fatty acid-based, and polyvinyl alcohol-based binders can be used.

The composition of the present disclosure may be in a dried form, or may be in a form including liquid or a form included in liquid. For example, the composition can take a form, such as powder, paste, or slurry. In addition, the composition may be a shaped body having a predetermined shape (hereinafter, referred to as a "first shaped body (first molding).")

The density of the first shaped body is preferably 2.75 g/cm$^3$ or higher, more preferably 2.80 g/cm$^3$ or higher, more preferably 2.85 g/cm$^3$ or higher, more preferably 2.90 g/cm$^3$ or higher, and further preferably 3.00 g/cm$^3$ or higher. The density can be calculated as (the mass of the first shaped body)/(the volume of the first shaped body), for example.

The first shaped body may have a layered structure of a plurality of compositions different in composition. Each layer in the layered body may be predominantly constituted of granules. The circularity of the granule in the composition in at least one layer of two adjacent layers, preferably, the circularity of the granule in the composition in two adjacent layers is preferably 0.81 or greater, more preferably 0.85 or greater, and further preferably 0.90 or greater.

If the circularity of the granule in the composition in one layer of two adjacent layers is 0.70 or smaller, the circularity of the granule in the composition in the other layer adjacent to said one layer is preferably 0.92 or greater and more preferably 0.95 or greater. If the circularity of the granule in the composition in one layer is greater than 0.70 and smaller than 0.81 (for example, 0.80 or smaller), the circularity of the granule in the composition in the other layer adjacent to said one layer is preferably 0.86 or greater, more preferably 0.90 or greater, and further preferably 0.94 or greater.

In the composition of the present disclosure, the sphericity of the granule is high. As such, when compositions are layered, particles of adjacent layers are readily mixed at the boundary between the layers. Therefore, even when a layered body is produced with compositions that have been produced independently of each other, or with compositions different in composition, detachment at the interface, and distortion and breakage due to distortion can be suppressed in a sintered body. In addition, when the color is different for each layer, the change in color over the boundary can be made smooth, thereby creating gradation.

Moreover, by increasing the sphericity of the granule, the filling density upon filling the composition into a mold can be increased. Due to this, the strength and the translucency of the sintered body can be enhanced. In addition, the filling density can be increased at a stage before pressing, and therefore, difference in the thickness between before the shaping and after the shaping can be made smaller, thereby facilitating the shaping. Even if the mold has a corner part, the filling property of the granule to the corner part can also be enhanced.

As a second embodiment, a method of producing the composition of the present disclosure will be described.

At first, zirconia and the stabilizer are mixed at a predetermined ratio to produce a mixture (mixing step). For example, when the stabilizer is yttria, the mixing ratio can be the same as the content of yttria described above. The mixing may be performed via dry mixing or wet mixing. The composition may be pulverized to a desired size (first pulverization step). The mixing step and the first pulverization step can be performed as the same step. Pulverization can be performed by, for example, dispersing the composition in a solvent, such as water (dispersion step), and subsequently using a ball mill. When the firing step and the following steps mentioned below are not performed, the composition is pulverized such that the average particle diameter thereof is, for example, 2.5 μm or smaller, preferably 1.5 μm or smaller, more preferably 0.14 μm or smaller, and further preferably 0.13 μm or smaller, in order to increase the sphericity of the granule. The composition may be dispersed by the pulverization. The average particle diameter can be measured via laser diffraction/scattering particle size distribution measuring method. After the mixing step and/or the first pulverization step, the composition is shaped into the form of a granule as mentioned above by drying the mixture via, for example, spray drying using a spray dryer (first drying step). As such, the composition of the present disclosure can be produced.

When the firing step and the following steps mentioned below are not performed, in the first pulverization step, the average particle diameter of the composition is made to be preferably less than 0.13 μm, more preferably 0.125 μm or less, more preferably 0.12 μm or less, and further preferably 0.115 μm or less. The average particle diameter of the composition of less than 0.13 μm can enhance the translucency of the sintered body.

When the firing step and the following steps mentioned below are not performed, it is preferred that a step of firing the composition at 700° C. or higher be not included prior to the step of producing the pre-sintered body and sintered body mentioned below. As such, production steps can be simplified, and forming a solid solution of the stabilizer with zirconia before sintering can also be suppressed.

It is preferred that zirconia and the stabilizer be prepared separately. For example, it is preferred that zirconia and the stabilizer be not deposited at the same time (in the same step), but that a step of preparing zirconia (for example, production step) and a step of preparing the stabilizer (for example, production step) be separate steps independent of each other. As such, the stabilizer can also be prevented from forming a solid solution with zirconia in a production step for the pre-sintered body mentioned below.

The following steps can be optionally conducted depending on the utilization purpose of the composition. For example, after any step of the steps mentioned above, the mixture and/or the composition may be fired (firing (calcination) step). As mentioned above, it is preferred that firing conditions be those such that the predominant crystal system of zirconia when cooling after firing does not become tetragonal and cubic crystals. In addition, it is preferred that the firing conditions be those such that at least a portion of the stabilizer does not form a solid solution with zirconia. For example, the firing temperature is preferably 700° C. or higher and more preferably 800° C. or higher. In addition, the firing temperature is preferably 1100° C. or lower, more preferably 1000° C. or lower, more preferably 980° C. or lower, and further preferably 950° C. or lower. Firing may be performed under the atmospheric air. By performing the firing step, it is believed that a portion of the stabilizer can form a solid solution with zirconia, that the stabilizer can be made easy to form a solid solution with zirconia in the sintering step, or that properties of the sintered body can be improved.

Simultaneously with any of the steps mentioned above, or after any of the steps, the composition may be dispersed in a solvent, such as water, to produce slurry, and additives, such as binders or coloring agents, may be added to the composition (dispersion and addition step). When neither a second pulverization step nor a second drying step, mentioned below, are performed, the dispersion and addition step may be performed anywhere from the mixing step to the first drying step mentioned above. Next, the composition can be pulverized until a desired size is attained (second pulverization step). The dispersion and addition step and the second pulverization step may be performed as the same step. The second pulverization step may be performed in the same manner as the first pulverization step. It is preferred that the composition be pulverized such that the average particle diameter as shown in the first pulverization step is achieved. After the addition step and/or the second pulverization step, the composition may be shaped into the form of a granule as mentioned above by drying the mixture via, for example, spray drying using a spray dryer (second drying step).

At a stage where granules have not been formed, before the first drying step or the second drying step, it is preferred that secondary particles be not formed in order to increase the sphericity of the granule, as mentioned above. Secondary particles have an irregular shape, and thus tend to make the sphericity of the granule lowered. In addition, it is preferred that the average particle diameter of particles constituting the granule be made small.

In the first drying step or the second drying step, it is preferred to reduce the amount of air bubbles in the slurry and to make the size of air bubbles smaller. This is because air bubbles form holes on the surface of the granule, thereby decreasing the sphericity. As a method of reducing the amount and size of air bubbles, a dispersing agent can be added to the slurry. Alternatively, by lowering the viscosity (value) and surface tension of the slurry, the amount and size of air bubbles can be reduced as well.

Zirconia powder with which yttria forms a solid solution is typically produced via coprecipitation method and hydrolysis method. In the coprecipitation method and hydrolysis method, a mixture of hydrous zirconia and yttria is produced from zirconium oxychloride and yttrium chloride in the same step, and the mixture is fired at 800° C. to 900° C. to produce stabilized zirconia powder with which yttria (yttrium) forms a solid solution. This yttria-doped zirconia is predominantly tetragonal crystal and/or cubic crystal. The particle diameter of zirconia powder obtained from the above is at a size level of several decades nm. In order to make this zirconia powder a raw material for a zirconia sintered body, the fired object is pulverized to a certain particle diameter and is then granulated to produce a composition.

The composition as produced by such a coprecipitation method or hydrolysis method has a high temperature dependence of the shrinkage factor at a temperature range for producing a pre-sintered body. In addition, when the firing time is short, it is not possible to obtain a sintered body with a sufficient translucency.

In the production method of the present disclosure, after producing zirconia (monoclinic), a stabilizer (yttria) is additionally mixed, and the stabilizer forms a solid solution with zirconia basically in a sintering step to produce a solid solution. As such, the temperature dependence of the shrinkage factor at the temperature range for producing the pre-sintered body can be lowered. In addition, a sintered body with a high translucency can be obtained even by sintering for a short time.

Moreover, in the production method of the present disclosure, when the firing step, the second pulverization step and the second drying step are not performed, the production costs of the composition can be cut down due to major time reduction. In addition, by appropriating facilities and time, by which the second pulverization step and the second drying step are performed, for the first pulverization step and the first drying step, the quantity of production per time can be doubled. Furthermore, by omitting the second pulverization step and the second drying step, occasions to contaminating the composition with impurities, such as wastes, can be reduced.

The composition may be shaped into a first shaped body (first molding) (first shaping step). Shaping methods are not limited to particular methods, and suitable methods may be appropriately selected depending on the purpose. For example, the composition may be shaped via methods, such as pressing, injection molding, and laser beam lithography. Alternatively, multi-stage shaping may be performed. For example, the composition may be press-shaped, and then, further subjected to CIP process. In addition, upon the shaping, the air pressure in the mold may be the atmospheric pressure, or may be reduced (which does not mean pressure change due to a press, etc.) For example, a shaped body with a higher compactness can be produced by reducing the pressure in the mold using a vacuum pump upon pressing. Due to this, the strength and the translucency of the sintered body can be enhanced.

The first shaped body may also be produced by layering compositions different in composition. For example, after the firing step, the composition is divided into a plurality of portions. Next, for each portion of the composition, additives are added separately. Then, for each portion of the composition, the pulverization step and the drying step are independently performed. As such, a plurality of compositions different in composition can be obtained. Next, each composition is put into a mold sequentially, thereby producing a layered body of a plurality of compositions (layering step). At this time, pressing should not be performed for every addition of compositions. This is to make compositions partially mixed readily at the interfacial region between layers. For every layering of compositions, and/or after all compositions are layered, the mold is vibrated (vibration step). A method of the vibration may be any scheme. For example, vibration may be applied to the layered body by tapping the mold or moving it up and down. Then, the first shaping step may be performed to produce the first shaped body having a layered structure. According to this method, each layer is produced from the identical composition, the circularity of the granule in two adjacent layers are substantially equal.

Even when two layers different in circularity are layered, after the layering step, compositions of both layers at the interfacial region between the layers can be mixed by performing the vibration step before the first shaping step.

The circularity of the granule in each layer can be the same as that of the first shaped body mentioned above.

The additives mentioned above may be appropriately added in any step.

According to the method of producing a composition of the present disclosure, a composition in the form of a granule having a high sphericity can be produced.

As a third embodiment, a zirconia pre-sintered body of the present disclosure will be described. The pre-sintered body may be a precursor (intermediate product) for a zirconia sintered body. In the present disclosure, the pre-sintered body can refer to, for example, those in which zirconia particles (powder) are formed into a block without being fully sintered. In particular, the pre-sintered body of the present disclosure refers to those produced from the composition of the present disclosure. It is preferred that the density of the pre-sintered body be 2.7 g/cm$^3$ or higher. In addition, the density of the pre-sintered body is preferably 4.0 g/cm$^3$ or lower, more preferably 3.8 g/cm$^3$ or lower, and further preferably 3.6 g/cm$^3$ or lower. When the density is within such a range, shaping process can be performed easily.

The content ratio of zirconia and the stabilizer in the pre-sintered body is the same as that in the composition before producing the pre-sintered body. From the viewpoint of strength and translucency of the sintered body produced from the pre-sintered body of the present disclosure, it is preferred that the stabilizer be yttria.

The percentage of not-doped stabilizer in the pre-sintered body depends on a firing temperature upon production of the pre-sintered body, but it is believed to be not more than the percentage of not-doped stabilizer in the composition before producing the pre-sintered body. The abundance of not-doped yttria in the pre-sintered body, $f_y$, can be calculated based on Expression 1 described above. The abundance of not-doped yttria in the pre-sintered body, $f_y$, can be the same as $f_y$ of the composition mentioned above.

In the pre-sintered body, the abundance of not-doped yttria, $f_y$, is preferably greater than 0%, more preferably 1% or greater, more preferably 2% or greater, and further preferably 3% or greater. The upper limit of the abundance of not-doped yttria, $f_y$, depends on the content by percentage of yttria in the pre-sintered body. When the content of yttria is 7.5 mol % or less based on the total amount of moles of zirconia and yttria, $f_y$ may be 15% or lower. For example, when the content of yttria is 3.5 mol % to 4.5 mol %, $f_y$ may be 7% or lower. When the content of yttria is 5 mol % to 6 mol %, $f_y$ may be 10% or lower. When the content of yttria is 5.5 mol % to 6.5 mol %, $f_y$ may be 11% or lower.

In the pre-sintered body, when the content of yttria is 3 mol % or more and less than 4.5 mol %, $f_y$ is preferably 2% or greater, more preferably 3% or greater, more preferably 4% or greater, and further preferably 5% or greater. When the content of yttria is 4.5 mol % or more and less than 5.8 mol %, $f_y$ is preferably 3% or greater, more preferably 4% or greater, more preferably 5% or greater, more preferably 6% or greater, and further preferably 7% or greater. When the content of yttria is 5.8 mol % or more and 7.5 mol % or less, $f_y$ is preferably 4% or greater, more preferably 5% or greater, more preferably 6% or greater, more preferably 7% or greater, and further preferably 8% or greater.

The crystal system of zirconia in the pre-sintered body depends on a firing temperature upon production of the pre-sintered body, but it is believed that the content ratio of monoclinic crystal is not more than the content ratio of monoclinic crystal in the composition before producing the pre-sintered body. The percentage of monoclinic system in zirconia, $f_m$, is preferably 60% or greater, more preferably 70% or greater, more preferably 80% or greater, more preferably 90% or greater, and further preferably 95% or greater based on the total amount of monoclinic system, tetragonal system and cubic system.

The flexural strength of the pre-sintered body is preferably 15 MPa or greater in order to ensure a strength that allows mechanical process. In addition, the flexural strength of the pre-sintered body is preferably 70 MPa or lower and more preferably 60 MPa or lower in order to facilitate mechanical process.

The flexural strength may also be measured in accordance with ISO 6872.

However, the size of the test piece is changed from the provision in JIS R1601 or ISO 6872 to be 5 mm×10 mm×50 mm. The surfaces and C plane of the test piece are subjected to surface finishing in the longitudinal direction using #600 sandpaper. The test piece is placed such that its broadest surface faces the vertical direction (loading direction). In the flexural test measurement, the span is 30 mm and the cross head speed is 0.5 mm/min.

A sintered body produced by firing the pre-sintered body for 30 minutes at a temperature of 1550° C. is called a first sintered body. A sintered body produced by firing the pre-sintered body for 120 minutes at a temperature of 1550° C. is called a second sintered body. When the translucency of the first sintered body and the second sintered body (see description below) are compared, the translucency of the first sintered body is preferably 85% or higher, more preferably 90% or higher, more preferably 95% or higher relative to the translucency of the second sintered body, and further preferably substantially equivalent to the translucency of the second sintered body.

The pre-sintered body may contain additives mentioned above.

The pre-sintered body may be a shaped body (molding) having a predetermined shape (hereinafter, referred to as a "second shaped body (second molding).") For example, the pre-sintered body may have a disc (circular plate) shape, rectangular parallelepiped shape, or shape of a dental product (for example, shape of a tooth crown). The pre-sintered body also includes dental products formed by processing a pre-sintered zirconia disc using a CAD/CAM (Computer-Aided Design/Computer-Aided Manufacturing) system (for example, prostheses with a shape of a tooth crown).

Next, as a fourth embodiment, a method of producing the pre-sintered body of the present disclosure will be described.

The pre-sintered body of the present disclosure can be produced by firing the first shaped body produced in the first shaping step described above at a temperature not leading to sintering of zirconia particles (that is, pre-sintering) (pre-sintering step). In order to ensure shaping into a block for handling, the firing temperature is, for example, preferably 800° C. or higher, more preferably 900° C. or higher, and further preferably 950° C. or higher. In addition, in order to enhance dimensional accuracy, the firing temperature is, for example, preferably 1200° C. or lower, more preferably 1150° C. or lower, and further preferably 1100° C. or lower.

It is believed that such a firing temperature does not advance forming a solid solution of the stabilizer.

The pre-sintered body can be shaped into a second shaped body (second molding)(second shaping step). Shaping methods are not limited to particular methods, and suitable methods can be appropriately selected depending on the purpose. For example, the second shaped body can be produced by subjecting a zirconia disc, which is also a pre-sintered body, to cutting process using a CAD/CAM system and making it into a shape of a dental product (for example, prosthesis with a shape of tooth crown).

As a fifth embodiment, a sintered body of the present disclosure will be described. In the present disclosure, the sintered body can refer to, for example, those in which zirconia particles (powder) have reached a sintered state. In particular, the sintered body of the present disclosure refers to those produced from the composition and/or pre-sintered body of the present disclosure. It is preferred that the relative density of the sintered body be 99.5% or more. The relative density can be calculated as the percentage of the measured density measured via Archimedes method to the theoretical density.

The zirconia sintered body of the present disclosure includes not only a sintered body formed by sintering shaped zirconia particles under ordinary pressure or without pressurization, but also a sintered body compacted by high temperature pressurization process, such as hot isostatic pressing (HIP) process.

The content ratio of zirconia and the stabilizer in the sintered body is the same as that of the composition and/or pre-sintered body before producing the sintered body. As for the crystal system of zirconia in the sintered body, the percentage of monoclinic system, $f_m$, is preferably 10% or lower, more preferably 5% or lower, and further preferably it is not contained substantially. Crystal systems other than monoclinic system are tetragonal crystal and/or cubic crystal.

As for the percentage of the stabilizer which forms a solid solution in the sintered body, it is preferred that 95% or more of the contained stabilizer form a solid solution with zirconia, and it is more preferred that substantially all of the stabilizer form a solid solution. The abundance of not-doped yttria, $f_y$, is preferably 5% or lower, more preferably 1% or lower, and further preferably substantially all yttria form a solid solution (0%).

The translucency of the sintered body is preferably 12 or higher, preferably 14 or higher, more preferably 15 or higher, and further preferably 16 or higher. The translucency herein means a value obtained by subtracting a second L* value from a first L* value, wherein, regarding the L* value of lightness (color space) in L*a*b* color system (JIS Z8781), the first L* value is a L* value measured for a sample with a thickness of 1.2 mm underlaid by white color, and the second L* value is a L* value measured for the same sample as that for measurement of the first L* value, underlaid by black color. As for a method of producing the sample, at first, granules (composition) can be subjected to press shaping, followed by CIP shaping, such that the thickness of the sintered body is 1.2 mm, to produce, for example, a circular plate shaped body with a diameter of 19 mm. Next, the shaped body can be fired under predetermined firing conditions to produce a sintered body with a thickness of 1.2 mm, which is used as the sample. For the measurement of the L* value, L* values with black color background and white color background can be measured by applying contact liquid to the surface of the sample and subsequently using a spectrophotometer (for example, CE100, analytical software Crystaleye (manufactured by Olympus Corporation)). As the contact liquid, for example, those having a refractive index nD, measured at a measurement wavelength of 589 nm (sodium D line), of 1.60 can be used.

The sintered body may contain additives mentioned above.

The sintered body may be a shaped body having a predetermined shape (hereinafter, referred to as a "third shaped body."). For example, the sintered body may have a disc (circular plate) shape, rectangular parallelepiped shape, or shape of a dental product (for example, shape of a tooth crown).

Next, as a sixth embodiment, a method of producing the sintered body of the present disclosure will be described.

The sintered body of the present disclosure can be produced by firing the composition (including the first shaped body) and/or the pre-sintered body (including the second shaped body) of the present disclosure at a temperature leading to sintering of zirconia particles (sintering step). The firing temperature is, for example, preferably 1400° C. or higher and more preferably 1450° C. or higher. In addition, the firing temperature is, for example, preferably 1650° C. or lower and more preferably 1600° C. or lower. It is preferred that the temperature rising rate and the temperature dropping rate be 300° C./min or less.

In the sintering step, the retention time at a temperature allowing sintering (for example, the highest firing temperature) is preferably shorter than 120 minutes, more preferably 90 minutes or shorter, more preferably 75 minutes or shorter, more preferably 60 minutes or shorter, more preferably 45 minutes or shorter, and further preferably 30 minutes or shorter. The retention time is preferably 1 minute or longer, more preferably 5 minutes or longer, and further preferably 10 minutes or longer. According to the production method of the present disclosure, even such a firing time can suppress decline in the translucency of the sintered body to be produced. In addition, by shortening the firing time, the production efficiency can be enhanced and the energy costs can also be reduced.

In the sintering step, the retention time at a temperature allowing sintering (for example, the highest firing temperature) can also be, for example, 25 minutes or shorter, 20 minutes or shorter, or 15 minutes or shorter.

It is preferred that the temperature rising rate and the temperature dropping rate in the sintering step be set such that the time required for the sintering step is short. For example, the temperature rising rate can be set such that the highest firing temperature is reached in the shortest time depending on capacity of the firing furnace. The temperature rising rate to the highest temperature can be, for example, 10° C./min or more, 50° C./min or more, 100° C./min or more, 120° C./min or more, 150° C./min or more, or 200° C./min or more. It is preferred that the temperature dropping rate be set as a rate that does not cause defects, such as cracks, in the sintered body. For example, after heating is completed, the sintered body can be allowed to cool at room temperature.

In the production method of the present disclosure, it is believed that the stabilizer (for example, yttria) forms a solid solution with zirconia in the sintering step to form a solid solution.

The sintered body can be shaped into a third shaped body (third shaping step). Shaping methods are not limited to particular methods, and suitable methods can be appropriately selected depending on the purpose. For example, the third shaped body can be produced by subjecting a zirconia block, which is also a sintered body, to cutting process using a CAD/CAM system and making it into a shape of a dental product (for example, prosthesis with a shape of tooth crown).

As a seventh embodiment, a dental product of the present disclosure will be described. The dental product of the present disclosure comprises the zirconia sintered body according to the fifth embodiment. The zirconia sintered body may have, for example, a shape of a tooth crown. The dental product may further comprise a porcelain material layered on the zirconia sintered body. The porcelain material can be ceramics, such as a glass material. Examples of the dental product may include prostheses (for example, ceramic frame, full contour crown), orthodontic products (for example, orthodontic bracket), dental implant products (for example, dental implant abutment).

Next, as an eighth embodiment, a method of producing the dental product of the present disclosure will be described. The dental product can be produced by sintering the composition (including the first shaped body) and/or the pre-sintered body (including the second shaped body) of the present disclosure, having a predetermined shape. Alternatively, the dental product can be produced by subjecting the sintered body of the present disclosure to cutting process (including the third shaped body).

A dental product having a porcelain material can be produced by, for example, a step of applying a slurry containing the porcelain material onto the sintered body, and a step of firing the sintered body onto which the porcelain material has been applied, to baking the porcelain material on the sintered body.

According to the third to eighth embodiments, a pre-sintered body, a sintered body, and a dental product having at least one of the advantages mentioned above can be obtained. For example, a pre-sintered body, a sintered body, and a dental product having a beautiful gradation can be obtained. A pre-sintered body, a sintered body, and a dental product having a high strength and translucency can be obtained. A pre-sintered body, a sintered body, and a dental product in which defects, such as detachment between layers, are suppressed can be obtained. A pre-sintered body, a sintered body, and a dental product whose corner is densely formed in the same manner as other parts can be obtained.

Regarding to structures and characteristics of the composition, pre-sintered body, sintered body and layered body, other than those described in this document, it is believed that it is impossible or utterly impractical to directly define them based on analysis or the like at the time the present application was filed. As such, it is believed that when the structures and characteristics other than those described in this document are defined, definition by a production method is useful.

Examples of the present disclosure will be described below. The present invention is not limited to the following Examples.

EXAMPLES

[Test Examples 1 to 18] A zirconia sintered body having a layered structure was produced, and an influence of circularity on the binding state of two adjacent layers was investigated.

[Production of zirconia composition] Zirconia and yttria were mixed to produce a "mixture." The zirconium oxide and the yttria were produced in steps independent of each other. The additive ratio of yttria is shown in Table 1 to Table 18. The additive rate shown in Table 1 to Table 18 is the percentage of yttria based on the total amount of moles of zirconia and yttria. Subsequently, the mixture was wet pulverized using a ball mill until a predetermined particle diameter was reached. Next, the mixture was fired for 2 hours at 950° C. to produce a "fired object." Then, the fired object was wet pulverized using a ball mill. Next, to the pulverized object in the form of slurry, a binder and 0.01 mass % of a coloring agent were added, and the resultant mixture was then dried using a spray dryer to produce a composition. The composition was in the form of the "granule" of zirconia particles. A plurality of compositions different in circularity was produced. The circularity was controlled by controlling the abundance of secondary particles or the average particle diameter of the particles constituting the granule in the firing step or the pulverization step, or by adjusting the amount and size of air bubbles in the slurry, and the viscosity and surface tension of the slurry. The coloring agent was added to make the color of the layered compositions different from each other, in order to check the mixed state at the boundary. The circularity of each composition in the form of a granule was measured using a flow particle image analyzer, FPIA-3000, manufactured by Sysmex Corporation. The measurement conditions were as follows: counting system: quantitative counting, objective lens: tenfold, optical system: bright field. The circularity was calculated as the average value of 30,000 or more granules.

[Production of zirconia sintered body] Next, a first composition, which was to be a first layer, was placed in a mold. Then, a second composition was placed on the first layer, and the mold was vibrated with a vibration device in order to mix the first composition and the second composition at the interface between the first layer and the second layer. Next, the layered body in the mold was pressurized with 981 N/cm$^2$ for shaping. Subsequently, the shaped body was subjected to CIP process. The thickness of both of the first layer and the second layer after the shaping was 5 mm to 6 mm. Next, the shaped body was fired for 2 hours at a temperature of 1500° C. to produce a sintered body.

A test piece was cut perpendicularly to the interface between the first layer and the second layer with a diamond cutter. The boundary between the first layer and the second layer on the cut section was observed with a stereoscopic microscope, and the mixing degree of the first composition and the second composition was evaluated based on the mixed state of the colors of the first layer and the second layer, on the basis of the following criteria.

A: The boundary between the first layer and the second layer is not clear, and the first composition and the second composition are uniformly mixed.

B: The boundary between the first layer and the second layer is recognizable, and the mixing of the first composition and the second composition is insufficient.

C: The boundary between the first layer and the second layer is clear, and the mixing of the first composition and the second composition cannot be confirmed.

A test piece was cut perpendicularly to the interface between the first layer and the second layer with a diamond cutter. After polishing the cut section, the polished surface was observed with a scanning electron microscope, and the detachability was evaluated on the basis of the following criteria.

A: No detachment is found between the first layer and the second layer.

B: Partial detachment is found between the first layer and the second layer.

A: Detachment is found between the first layer and the second layer.

When the circularity of one layer is low, for example, when the circularity of one layer is 0.7 or smaller, as long as the circularity of the other layer is 0.85 or greater, in particular, greater than 0.91, at least one of the mixing degree and the detachability was able to be evaluated as A in most Test Examples. In addition, even when the circularity of one layer is 0.7 or smaller, as long as the circularity of the other layer is 0.95 or greater, both of the mixing degree and the detachability were able to be evaluated as A.

When the circularity of one layer is greater than 0.7, if the circularity of the other layer is greater than 0.8, in particular, 0.84 or greater, both of the mixing degree and the detachability were able to be evaluated as A.

TABLE 1

| | Content rate of yttria (mol %) | Circularity of First composition | Circularity of Second composition | Mixing degree | Detachability |
|---|---|---|---|---|---|
| Test Example 1-1 | 4 | 0.66 | 0.71 | C | C |
| Test Example 1-2 | | | 0.75 | C | C |
| Test Example 1-3 | | | 0.80 | C | B |
| Test Example 1-4 | | | 0.84 | B | A |
| Test Example 1-5 | | | 0.89 | B | A |
| Test Example 1-6 | | | 0.94 | A | A |
| Test Example 1-7 | | | 0.98 | A | A |

TABLE 2

| | Content rate of yttria (mol %) | Circularity of First composition | Circularity of Second composition | Mixing degree | Detachability |
|---|---|---|---|---|---|
| Test Example 2-1 | 4 | 0.71 | 0.75 | C | C |
| Test Example 2-2 | | | 0.80 | B | B |
| Test Example 2-3 | | | 0.84 | A | A |
| Test Example 2-4 | | | 0.89 | A | A |
| Test Example 2-5 | | | 0.94 | A | A |
| Test Example 2-6 | | | 0.98 | A | A |

TABLE 3

| | Content rate of yttria (mol %) | Circularity of First composition | Circularity of Second composition | Mixing degree | Detachability |
|---|---|---|---|---|---|
| Test Example 3-1 | 4 | 0.75 | 0.80 | B | B |
| Test Example 3-2 | | | 0.84 | A | A |
| Test Example 3-3 | | | 0.89 | A | A |
| Test Example 3-4 | | | 0.94 | A | A |
| Test Example 3-5 | | | 0.98 | A | A |

TABLE 4

| | Content rate of yttria (mol %) | Circularity of First composition | Circularity of Second composition | Mixing degree | Detachability |
|---|---|---|---|---|---|
| Test Example 4-1 | 4 | 0.80 | 0.84 | A | A |
| Test Example 4-2 | | | 0.89 | A | A |
| Test Example 4-3 | | | 0.94 | A | A |
| Test Example 4-4 | | | 0.98 | A | A |

TABLE 5

| | Content rate of yttria (mol %) | Circularity of First composition | Circularity of Second composition | Mixing degree | Detachability |
|---|---|---|---|---|---|
| Test Example 5-1 | 4 | 0.84 | 0.89 | A | A |
| Test Example 5-2 | | | 0.94 | A | A |
| Test Example | | | 0.98 | A | A |

TABLE 5-continued

| | Content rate of yttria (mol %) | Circularity of First composition | Circularity of Second composition | Mixing degree | De-tachability |
|---|---|---|---|---|---|
| 5-3 | | | | | |

TABLE 6

| | Content rate of yttria (mol %) | Circularity of First composition | Circularity of Second composition | Mixing degree | De-tachability |
|---|---|---|---|---|---|
| Test Example 6-1 | 4 | 0.89 | 0.94 | A | A |
| Test Example 6-2 | | | 0.98 | A | A |

TABLE 7

| | Content rate of yttria (mol %) | Circularity of First composition | Circularity of Second composition | Mixing degree | De-tachability |
|---|---|---|---|---|---|
| Test Example 7-1 | 5 | 0.64 | 0.70 | C | C |
| Test Example 7-2 | | | 0.74 | C | C |
| Test Example 7-3 | | | 0.80 | C | B |
| Test Example 7-4 | | | 0.85 | B | B |
| Test Example 7-5 | | | 0.91 | B | B |
| Test Example 7-6 | | | 0.95 | A | B |
| Test Example 7-7 | | | 0.98 | A | A |

TABLE 8

| | Content rate of yttria (mol %) | Circularity of First composition | Circularity of Second composition | Mixing degree | De-tachability |
|---|---|---|---|---|---|
| Test Example 8-1 | 5 | 0.70 | 0.74 | C | C |
| Test Example 8-2 | | | 0.80 | C | B |
| Test Example 8-3 | | | 0.85 | B | B |
| Test Example 8-4 | | | 0.91 | B | B |
| Test Example 8-5 | | | 0.95 | A | A |
| Test Example 8-6 | | | 0.98 | A | A |

TABLE 9

| | Content rate of yttria (mol %) | Circularity of First composition | Circularity of Second composition | Mixing degree | De-tachability |
|---|---|---|---|---|---|
| Test Example 9-1 | 5 | 0.74 | 0.80 | B | B |
| Test Example 9-2 | | | 0.85 | B | A |
| Test Example 9-3 | | | 0.91 | A | A |
| Test Example 9-4 | | | 0.95 | A | A |
| Test Example 9-5 | | | 0.98 | A | A |

TABLE 10

| | Content rate of yttria (mol %) | Circularity of First composition | Circularity of Second composition | Mixing degree | De-tachability |
|---|---|---|---|---|---|
| Test Example 10-1 | 5 | 0.80 | 0.85 | A | A |
| Test Example 10-2 | | | 0.91 | A | A |
| Test Example 10-3 | | | 0.95 | A | A |
| Test Example 10-4 | | | 0.98 | A | A |

TABLE 11

| | Content rate of yttria (mol %) | Circularity of First composition | Circularity of Second composition | Mixing degree | De-tachability |
|---|---|---|---|---|---|
| Test Example 11-1 | 5 | 0.85 | 0.91 | A | A |
| Test Example 11-2 | | | 0.95 | A | A |
| Test Example 11-3 | | | 0.98 | A | A |

TABLE 12

| | Content rate of yttria (mol %) | Circularity of First composition | Circularity of Second composition | Mixing degree | De-tachability |
|---|---|---|---|---|---|
| Test Example 12-1 | 5 | 0.91 | 0.95 | A | A |
| Test Example 12-2 | | | 0.98 | A | A |

TABLE 13

| | Content rate of yttria (mol %) | Circularity of First composition | Circularity of Second composition | Mixing degree | De-tachability |
|---|---|---|---|---|---|
| Test Example 13-1 | 6 | 0.65 | 0.69 | C | C |
| Test Example 13-2 | | | 0.76 | C | C |
| Test Example 13-3 | | | 0.79 | C | B |
| Test Example 13-4 | | | 0.85 | B | A |
| Test Example 13-5 | | | 0.91 | B | A |
| Test Example 13-6 | | | 0.96 | A | A |
| Test Example 13-7 | | | 0.98 | A | A |

TABLE 14

| | Content rate of yttria (mol %) | Circularity of First composition | Circularity of Second composition | Mixing degree | De-tachability |
|---|---|---|---|---|---|
| Test Example 14-1 | 6 | 0.69 | 0.76 | C | C |
| Test Example 14-2 | | | 0.79 | C | B |
| Test Example 14-3 | | | 0.85 | B | A |
| Test Example 14-4 | | | 0.91 | A | A |
| Test Example 14-5 | | | 0.96 | A | A |
| Test Example 14-6 | | | 0.98 | A | A |

TABLE 15

| | Content rate of yttria (mol %) | Circularity of First composition | Circularity of Second composition | Mixing degree | De-tachability |
|---|---|---|---|---|---|
| Test Example 15-1 | 6 | 0.76 | 0.79 | C | A |
| Test Example 15-2 | | | 0.85 | A | A |
| Test Example 15-3 | | | 0.91 | A | A |
| Test Example 15-4 | | | 0.96 | A | A |
| Test Example 15-5 | | | 0.98 | A | A |

TABLE 16

| | Content rate of yttria (mol %) | Circularity of First composition | Circularity of Second composition | Mixing degree | De-tachability |
|---|---|---|---|---|---|
| Test Example 16-1 | 6 | 0.79 | 0.85 | A | A |
| Test Example 16-2 | | | 0.91 | A | A |
| Test Example 16-3 | | | 0.96 | A | A |
| Test Example 16-4 | | | 0.98 | A | A |

TABLE 17

| | Content rate of yttria (mol %) | Circularity of First composition | Circularity of Second composition | Mixing degree | De-tachability |
|---|---|---|---|---|---|
| Test Example 17-1 | 6 | 0.85 | 0.91 | A | A |
| Test Example 17-2 | | | 0.96 | A | A |
| Test Example 17-3 | | | 0.98 | A | A |

TABLE 18

| | Content rate of yttria (mol %) | Circularity of First composition | Circularity of Second composition | Mixing degree | De-tachability |
|---|---|---|---|---|---|
| Test Example 18-1 | 6 | 0.91 | 0.96 | A | A |
| Test Example 18-2 | | | 0.98 | A | A |

[Measurement of Abundance of Not-Doped Yttria and Percentage of Monoclinic Crystal]

For the zirconia compositions used in Test Examples 1 to 6 and Test Examples 13 to 18, the abundance of not-doped yttria and the percentage of monoclinic crystal were measured. During the production steps for the zirconia composition in the form of a granule as described above, for compositions produced in each step (the mixture, the fired object, and the granule), XRD measurement was performed, and the abundance of not-doped yttria $f_y$ and the percentage of monoclinic crystal $f_m$ were calculated. The results are shown in Table 19.

In any of the steps, an XRD peak of yttria was observed. In Test Examples 1 to 6, where the additive rate of yttria was low, $f_y$ in the form of a granule was 2 or higher. In Test Examples 13 to 18, where the additive rate of yttria was high, $f_y$ in the form of a granule was 4 or higher. The $f_y$ decreases over the steps, but it is believed that this is because the crystal was destroyed due to the pulverization, thereby decreasing the relative peak of yttria to zirconia. However, this does not make a denial of possibility of decrease of $f_y$ due to forming a solid solution. It is believed that the percentage of not-doped yttria does not affect the mixing degree and the detachability.

The percentage of monoclinic crystal $f_m$ in the zirconia composition in the form of a granule with an yttria content of 4 mol % was 98%. The percentage of monoclinic crystal $f_m$ in the zirconia composition in the form of a granule with an yttria content of 6 mol % was 97%. As such, for the composition in the form of a granule, 90% or more of zirconia was monoclinic crystal. It is believed that by changing zirconia to be used as a raw material (for example, to zirconia having a different crystal system) or by changing conditions in the firing step, the percentage of monoclinic crystal in the yttria composition in the form of a granule can be made altered to 20% or more, 40% or more, 60% or more, or 80% or more. It is believed that the percentage of monoclinic crystal does not affect the mixing degree and the detachability.

TABLE 19

| | Additive rate of yttria (mol %) | Step | $f_y$ (%) | $f_m$ (%) |
|---|---|---|---|---|
| Test examples 1-6 | 4 | Mixture | 10.5 | 100 |
| | | Fired object | 3.8 | 94 |
| | | Granule | 2.9 | 98 |
| Test examples 13-18 | 6 | Mixture | 13.7 | 100 |
| | | Fired object | 9.3 | 99 |
| | | Granule | 4.7 | 97 |

Test Examples 19 to 39

[Measurement of Circularity, Angle of Repose, Average Particle Diameter, Untamped Density, and Tamped Density]

While changing the average particle diameter of zirconia particles constituting a granule, and the average particle diameter of granules, granules different in circularity were produced. For each granule, the circularity, the angle of repose, the average particle diameter, the untamped density, and the tamped density were measured. The production method of the composition is the same as that for Test Examples 1 to 18. The circularity was varied by changing the average particle diameter of constituent particles, as well as air bubbles in slurry or the viscosity of slurry, etc. The circularity of the granule was measured using a flow particle image analyzer, FPIA-3000, manufactured by Sysmex Corporation. The measurement conditions were as follows: counting system: quantitative counting, objective lens: ten-fold, optical system: bright field. The circularity was calculated as the average value of 30,000 or more granules. The angle of repose was measured in accordance with JIS R9301-2-2. The average particle diameter of granules was measured using Robot Shifter manufactured by SEISHIN ENTERPRISE Co., Ltd. The average particle diameter of particles constituting a granule was measured via laser diffraction/scattering particle size distribution measuring method. The untamped density and the tamped density were measured in accordance with JIS R9301-2-3. The results are shown in Table 20. FIGS. 5 to 7 show graphs on which the angle of repose, the untamped density, and the tamped density are plotted against the circularity.

Even with varied average particle diameters of constituent particles, the circularity was allowed to be 0.84 or greater, 0.9 or greater, and 0.94 or greater. The angle of repose was allowed to be 32° or smaller, 28° or smaller, 24° or smaller, and 22° or smaller. Referring to FIG. 5, it is found that as the circularity gets higher, the angle of repose tends to decline. The average particle diameter of granules was allowed to vary within the range of 10 μm to 200 μm. The untamped density was allowed to be 1.25 g/cm$^3$ or more. Referring to FIG. 6, it is found that as the circularity gets higher, the untamped density also tends to get higher. The tamped density was allowed to be 1.47 g/cm$^3$ or more. Referring to FIG. 7, it is found that as the circularity gets higher, the tamped density also tends to get higher. As such, it is believed that by increasing the circularity, the filling density can be increased.

TABLE 20

| | Circularity | Angle of repose (°) | Average particle diameter of granules (μm) | Average particle diameters of constituent particles (μm) | Untamped density (g/cm$^3$) | Tamped density (g/cm$^3$) |
|---|---|---|---|---|---|---|
| Test Example 19 | 0.847 | 24 | 12 | 0.012 | 1.35 | 1.49 |
| Test Example 20 | 0.903 | 24 | 11 | 0.011 | 1.37 | 1.55 |
| Test Example 21 | 0.948 | 21 | 10 | 0.012 | 1.39 | 1.64 |
| Test Example 22 | 0.852 | 26 | 25 | 0.051 | 1.33 | 1.48 |
| Test Example 23 | 0.899 | 23 | 21 | 0.055 | 1.34 | 1.51 |
| Test Example 24 | 0.947 | 22 | 26 | 0.059 | 1.38 | 1.63 |
| Test Example 25 | 0.855 | 28 | 30 | 0.12 | 1.27 | 1.50 |
| Test Example 26 | 0.901 | 24 | 29 | 0.11 | 1.32 | 1.56 |

TABLE 20-continued

| | Circularity | Angle of repose (°) | Average particle diameter of granules (μm) | Average particle diameters of constituent particles (μm) | Untamped density ($g/cm^3$) | Tamped density ($g/cm^3$) |
|---|---|---|---|---|---|---|
| Test Example 27 | 0.945 | 20 | 28 | 0.12 | 1.40 | 1.65 |
| Test Example 28 | 0.845 | 26 | 31 | 0.25 | 1.25 | 1.51 |
| Test Example 29 | 0.906 | 24 | 30 | 0.24 | 1.33 | 1.60 |
| Test Example 30 | 0.943 | 21 | 27 | 0.26 | 1.39 | 1.65 |
| Test Example 31 | 0.856 | 27 | 39 | 0.53 | 1.25 | 1.48 |
| Test Example 32 | 0.898 | 24 | 46 | 0.51 | 1.32 | 1.53 |
| Test Example 33 | 0.943 | 22 | 45 | 0.54 | 1.41 | 1.60 |
| Test Example 34 | 0.852 | 31 | 61 | 1.04 | 1.31 | 1.47 |
| Test Example 35 | 0.909 | 25 | 68 | 1.05 | 1.34 | 1.51 |
| Test Example 36 | 0.952 | 22 | 63 | 1.02 | 1.39 | 1.55 |
| Test Example 37 | 0.859 | 32 | 200 | 2.02 | 1.29 | 1.48 |
| Test Example 38 | 0.908 | 26 | 198 | 2.04 | 1.35 | 1.53 |
| Test Example 39 | 0.949 | 21 | 199 | 2.03 | 1.36 | 1.59 |

Test Example 40

[Observation with Electron Microscope]

As for granules of Example 20, their shapes were observed using a field emission scanning electron microscope (FE-SEM). FIG. 1 shows a micrograph thereof. In addition, the shape of particles constituting the granule was also observed. FIG. 2 shows a micrograph thereof. As a comparison contrast, granules and particles constituting the granule were also observed for TZ-3YSB-E manufactured by TOSOH CORPORATION. FIG. 3 and FIG. 4 show micrographs thereof.

For the granule shown in FIG. 1, the shape of the granule appears to be spherical (perfect sphere), and it is found that the sphericity (circularity) is high. For the particles constituting the granule, shown in FIG. 2, many particles were primary particles that appear to be separable, ant the number of secondary particles formed of aggregated primary particles was few. On the other hand, for the granule shown in FIG. 3, the shape of the granule is non-spherical (irregular shape), and it is found that the sphericity (circularity) is low. The particles constituting the granule, shown in FIG. 4, are secondary particles in which primary particles are aggregated in an inseparable manner (secondary particles formed by melting and binding a plurality of primary particles). The granule shown in FIG. 1 is predominantly constituted with primary particles. On the other hand, the granule shown in FIG. 3 is predominantly constituted with distorted secondary particles. It is believed that because of this, a difference in the sphericity of the granule was generated.

The composition, pre-sintered body and sintered body, and the production method thereof, as well as the layered body, according to the present invention have been described based on the embodiments and Examples described above; however, the present invention is not limited to the embodiments and Examples described above, and various modifications, alterations and improvements to each of the disclosed elements (including elements described in claims, description and drawings) can be included within the scope of the present invention and based on the basic, technical ideas of the present invention. In addition, within the scope of the claims of the present invention, a variety of combinations, substitutions and selections of disclosed elements are possible.

Further problems, objects and embodiments (including modifications) are also revealed from the entire disclosed matters of the present invention including the claims.

Even in the case where there is no particular description, numerical ranges described in this specification should be construed as that any numerical value and range included within those ranges is specifically described in the specification.

INDUSTRIAL APPLICABILITY

The composition, pre-sintered body and sintered body, and the production method thereof, as well as the layered body, according to the present disclosure can be utilized in various applications: dental materials, such as prostheses; connecting components for optical fibers, such as ferrules or sleeves; various kinds of tools (for example, pulverizing balls, grinding tools); various kinds of components (for example, screws, bolts and nuts); various kinds of sensors; components for electronics; decorative materials (for example, watch bands); and the like. When the composition, pre-sintered body and sintered body are used for dental materials, they can be used for, for example, a coping, framework, crown, crown & bridge, abutment, implant, implant screw, implant fixture, implant bridge, implant bar, bracket, denture base, inlay, anlay, onlay, orthodontic wire, laminate veneer and the like.

What is claimed is:

1. A composition, comprising:

granules comprising aggregated zirconia particles, wherein the granules have an average circularity of 0.81 or greater, based on a projected image, and wherein a zirconia crystal system of the zirconia particles has 20% or more of a monoclinic system.

2. The composition of claim 1, having an angle of repose, measured in accordance with JIS R9301-2-2, in a range of from 20 degrees to 35 degrees.

3. The composition of claim 1, having an untamped density, measured in accordance with JIS R9301-2-3, of 1.2 $g/cm^3$ or more.

4. The composition of claim 1, having a tamped density, measured in accordance with JIS R9301-2-3, of 1.3 $g/cm^3$ or more.

5. The composition of claim 1, wherein an average particle diameter of the zirconia particles is in a range of from 0.01 μm to 2.5 μm.

6. The composition of claim 1, wherein a BET specific surface area of the zirconia particles is in a range of from 7.5 $m^2/g$ to 25 $m^2/g$.

7. The composition of claim 1, wherein an average particle diameter of the granules is in a range of from 10 μm to 200 μm.

8. The composition of claim 1, further comprising:

a stabilizer capable of suppressing phase transition of zirconia.

9. The composition of claim 8, wherein a portion of the stabilizer does not form a solid solution with the zirconia.

10. The composition of claim 8, wherein the stabilizer is yttria.

11. The composition of claim 10, wherein the composition comprises the yttria in a range of from 3 mol % to 7.5 mol %, based on a total amount of moles of the zirconia and the yttria.

12. The composition of claim 1, further comprising:

a binder and/or a dispersing agent.

13. The composition of claim 2, having an untamped density, measured in accordance with JIS R9301-2-3, of 1.2 $g/cm^3$ or more.

14. The composition of claim 2, having a tamped density, measured in accordance with JIS R9301-2-3, of 1.3 $g/cm^3$ or more.

15. The composition of claim 3, having a tamped density, measured in accordance with JIS R9301-2-3, of 1.3 $g/cm^3$ or more.

16. The composition of claim 14, having a tamped density, measured in accordance with JIS R9301-2-3, of 1.3 $g/cm^3$ or more.

17. The composition of claim 2, wherein an average particle diameter of the zirconia particles is in a range of from 0.01 μm to 2.5 μm.

18. The composition of claim 16, wherein an average particle diameter of the zirconia particles is in a range of from 0.01 μm to 2.5 μm.

19. The composition of claim 18, wherein a BET specific surface area of the zirconia particles is in a range of from 7.5 $m^2/g$ to 25 $m^2/g$.

20. The composition of claim 19, wherein an average particle diameter of the granules is in a range of from 10 μm to 200 μm.

* * * * *